United States Patent
Celik et al.

(10) Patent No.: US 8,798,713 B2
(45) Date of Patent: Aug. 5, 2014

(54) MAGNETIC RESONANCE METHOD AND APPARATUS TO SEPARATE DEPICTION OF A TRACKED ITEM FROM SURROUNDING ANATOMY OF A PATIENT, USING A TRANSMIT ARRAY SYSTEM

(76) Inventors: Haydar Celik, Toronto (CA); Ergin Atalar, Ankara (TR)

(*) Notice: Subject to any disclaimer, the term of this patent is extended or adjusted under 35 U.S.C. 154(b) by 557 days.

(21) Appl. No.: 13/087,621

(22) Filed: Apr. 15, 2011

(65) Prior Publication Data

US 2011/0257516 A1 Oct. 20, 2011

Related U.S. Application Data

(60) Provisional application No. 61/325,187, filed on Apr. 16, 2010.

(51) Int. Cl.
*A61B 5/055* (2006.01)

(52) U.S. Cl.
USPC .............. 600/411; 600/423; 600/424

(58) Field of Classification Search
USPC .......... 600/410, 411, 422, 423, 424; 324/307, 324/309, 318, 322
See application file for complete search history.

(56) References Cited

U.S. PATENT DOCUMENTS

2008/0319301 A1* 12/2008 Busse .................... 600/410
2010/0249572 A1* 9/2010 Weiss .................... 600/410

OTHER PUBLICATIONS

Celik et al , "A Novel Catheter Tracking Method Using Reversed Polarization", 2006, Proc. Intl. Soc. Mag. Reson. Med. vol. 14, p. 264.*
Celik et al., "A Catheter Tracking Method Using Reverse Polarization for MR-Guided Interventions" Magnetic Resonance in Medicine, vol. 58, pp. 1224-1231 (2007).

* cited by examiner

*Primary Examiner* — Ruth S Smith
(74) *Attorney, Agent, or Firm* — Schiff Hardin LLP (57) ABSTRACT

In a method for detecting rotational orientation and position tracking of an inductively coupled RF (ICRF) coil using a transmit array system, a conventional body birdcage coil is used, but the quadrature hybrid is eliminated to use the two excitation-channels separately. The transmit array system provides RF excitations such that the body birdcage coil creates linearly polarized and circulating RF pulses instead of a conventional rotational forward polarized excitation. Inductively coupled RF (ICRF) coils can be constructed on catheters for detecting rotational orientation and tracking purposes. The modifications on anatomy and ICRF coil images are different due to the RF excitation scheme such that the ICRF coil can be separated from the anatomy in real-time. After separating the ICRF coil from the anatomy, a color-coded image can be reconstructed, for example.

12 Claims, 6 Drawing Sheets

MAGNETIC RESONANCE METHOD AND APPARATUS TO SEPARATE DEPICTION OF A TRACKED ITEM FROM SURROUNDING ANATOMY OF A PATIENT, USING A TRANSMIT ARRAY SYSTEM

RELATED APPLICATION

The present application claims the benefit of the filing date of provisional application 61/325,187, filed Apr. 16, 2010.

BACKGROUND OF THE INVENTION

1. Field of the Invention

The present invention concerns a method employing the acquisition of magnetic resonance data to track an item, such as a catheter, using a transmit array system of a magnetic resonance data acquisition unit. More specifically, the method concerns tracking the rotational orientation and position of the item, and separating the item from the surrounding anatomy in the resulting magnetic resonance image or spectroscopic data.

2. Description of the Prior Art

A precise and fast localization of interventional devices is a necessity to perform minimally invasive operations. Generally, X-ray imaging is used for these operations due to almost perfect instrument visualization and determination of catheter orientation. X-ray imaging, however, cannot provide soft tissue contrast, and ionizing radiation is exposed to patients as well as staff.

On the other hand, MRI is a non-ionizing imaging modality that offers impressive soft tissue contrast as compared to X-ray imaging. One of the main challenging problems in MR-guided interventions is the difficulty in real-time detection and tracking of the interventional devices, such as catheters, guidewires, and biopsy needles. Various techniques have been developed for identification of interventional devices. Although, the passive and active catheter tracking methods have distinct advantages, the passive tracking methods have reliability problems (Kochli V D, McKinnon G C, Hofmann E, Vonschulthess G K. Vascular Interventions Guided by Ultrafast Mr-Imaging—Evaluation of Different Materials. Magnetic Resonance in Medicine 1994; 31(3): 309-314), and device handling in the active tracking techniques is not easy. There are also hybrid methods and they make use of an inductively coupled RF (ICRF) (Quick H H, Zenge M O, Kuehl H, Kaiser G, Aker S, Massing S, Bosk S, Ladd M E. Interventional magnetic resonance angiography with no strings attached: Wireless active catheter visualization. Magnetic Resonance in Medicine 2005; 53(2):446-455; Celik H, Uluturk A, Tali T, Atalar E. A catheter tracking method using reverse polarization for MR-guided interventions. Magn Reson Med 2007; 58(6):1224-1231) coil. Even though many researchers introduced solutions for tracking problem of interventional devices such as biopsy needles and catheters, rotational orientation of a catheter is a relatively untouched subject.

In all of the applications and methods mentioned above, conventional imaging systems have been used. On the other hand transmit array systems have recently been introduced for experimental studies. Yet these studies are mostly concentrated on understanding the working principles, exploring the capabilities of the system, and homogenizing the high frequency $B_1$ fields (Katscher U, Börnert P, Leussler C, van den Brink J S. Transmit SENSE. Magnetic Resonance in Medicine 2003; 49(1):144-150; Adriany G, Van de Moortele P F, Wiesinger F, Moeller S, Strupp J P, Andersen P, Snyder C, Zhang X, Chen W, Pruessmann K P, Boesiger P, Vaughan T, Uğurbil K. Transmit and receive transmission line arrays for 7 Tesla parallel imaging. Magnetic Resonance in Medicine 2005; 53(2):434-445. Pinkerton R G, Near J P, Barberi E A, Menon R S, Bartha R. Transceive surface coil array for MRI of the human prostate at 4T. Magnetic Resonance in Medicine 2007; 57(2):455-458). Although usage of transmit array systems has been limited, the use of transmit array system was recently introduced in our previous study to obtain reverse polarization during transmission.

SUMMARY OF THE INVENTION

In accordance with the present invention, a transmit array system is used to i) detect rotational orientation and ii) track position of interventional devices on which ICRF coils are constructed. Conventional RF excitation pulses are modified such that circulating linearly polarized $B_1$ fields are created instead of forward polarized magnetic field. Furthermore direction of the linearly polarized magnetic field vectors are changed such that resultant anatomy image shifts in phase encoding direction but two copies of ICRF coil image are created and they shift in both the phase encoding and the opposite directions. Moreover, the ICRF coil images have phase difference directly proportional to rotational orientation of the ICRF coil. As a result, the method enables simultaneous acquisition of the anatomy and ICRF coil images with rotational orientation information. This novel method can be used in applications in which asymmetric catheter design is important such as MR-guided intravascular focused ultrasound (IVUS) (Hwang J H, Zhou Y, Warren C, Brayman A A, Crum L A. Targeted Venous Occlusion Using Pulsed High-Intensity Focused Ultrasound. Biomedical Engineering, IEEE Transactions on 2010; 57(1):37-40. Di Mario C, Gorge G, Peters R, Kearney P, Pinto F, Hausmann D, von Birgelen C, Colombo A, Mudra H, Roelandt J, Erbel R. Clinical application and image interpretation in intracoronary ultrasound. Study Group on Intracoronary Imaging of the Working Group of Coronary Circulation and of the Subgroup on Intravascular Ultrasound of the Working Group of Echocardiography of the European Society of Cardiology. Eur Heart J 1998; 19(2):207-229) with independent transducer arrays (Fronheiser M P, Light E D, Smith S W. Real-time 3D ultrasound with multiple transducer arrays. 2004. p 786-789 Vol. 781) and RF ablation.

BRIEF DESCRIPTION OF THE DRAWINGS

FIGS. 7a, 7b and 7c show images obtained in accordance with the inventive method with water-filled straws used as a phantom in the oil bath of FIG. 6a.

DESCRIPTION OF THE PREFERRED EMBODIMENTS

Basic Operation of a Magnetic Resonance Imaging Apparatus

Figure 1:
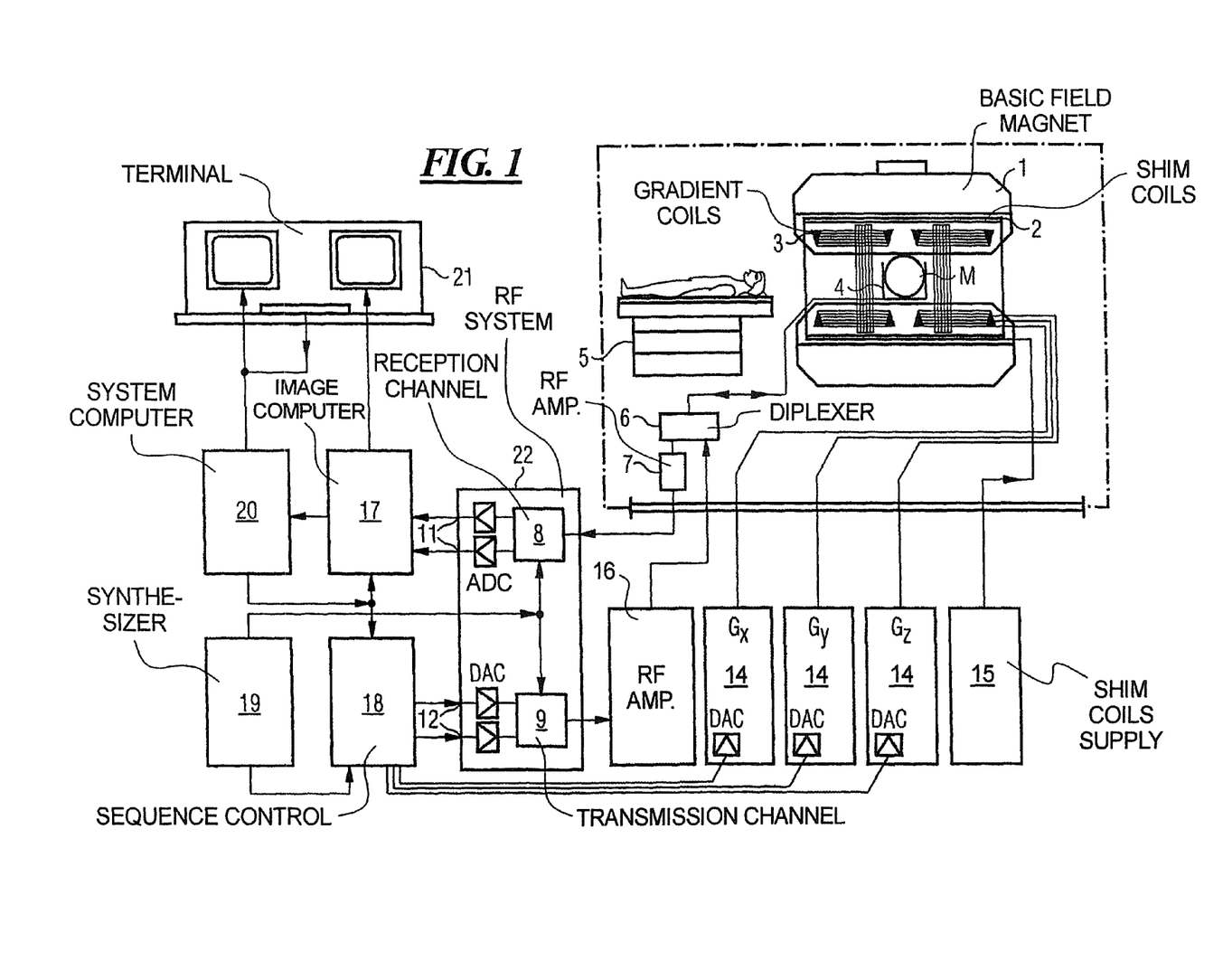
FIG. 1 schematically illustrates the basic components of a magnetic resonance imaging apparatus for implementing an embodiment of the inventive method.

FIG. 1 schematically illustrates a magnetic resonance tomography apparatus in which gradient pulses according to the present invention are generated. The design of the magnetic resonance tomography apparatus corresponds a conventional tomography apparatus, with the exceptions discussed below. A basic field magnet 1 generates a temporally constant strong magnetic field for polarization or alignment of the nuclear spins in the examination region of the subject such as, for example, a part of a human body to be examined. The high homogeneity of the basic magnetic field necessary for the magnetic resonance data acquisition is defined in a spherical measurement volume M in which the parts of the human body to be examined are introduced. For support of the homogeneity requirements, and in particular for elimination of temporally invariable influences, shim plates made from ferromagnetic material are mounted at a suitable location. Temporally variable influences are eliminated by shim coils 2 that are activated by a shim current supply 15.

A cylindrical gradient coil system 3 that is composed of three coils (windings) is used in the basic field magnet 1. Each coil is supplied with current by an amplifier 14 for generation of a linear gradient field in the respective direction of the Cartesian coordinate system. The first coil of the gradient field system 3 generates a gradient $G_x$ in the x-direction, the second coil generates a gradient $G_y$ in the y-direction and the third coil generates a gradient $G_z$ in the z-direction. Each amplifier 14 has a digital-analog converter that is activated by a sequence controller 18 for time-accurate generation of the gradient pulses.

Located within the gradient field system 3 is a radio-frequency antenna 4 that converts the radio-frequency pulses emitted by a radio-frequency power amplifier 16 into a magnetic alternating field for excitation of the nuclei and alignment of the nuclear spins of the subject to be examined, or of the region of the subject to be examined. The alternating field originating from the precessing nuclear spins (i.e. normally the nuclear spin echo signals caused by a pulse sequence composed of one or more radio-frequency pulses and one or more gradient pulses) is also converted by the radio-frequency antenna 4 into a voltage that is supplied via an amplifier 7 to a radio-frequency receiver channel 8 of a radio-frequency system 22. The radio-frequency system 22 furthermore has a transmission channel 9 in which are generated the radio frequency pulses for the excitation the nuclear spins. The respective radio-frequency pulses are digitally represented as a series of complex numbers conforming to a pulse sequence predetermined in the sequence controller 18 by the system computer 20. This number series is supplied as a real part and an imaginary part via respective inputs 12 to a digital-analog converter (DAC) in the radio-frequency system 22 and, from this, to a transmission channel 9. In the transmission channel 9, the pulse sequences are modulated with a radio-frequency carrier signal whose base frequency corresponds to the resonance frequency of the nuclear spins in the measurement volume.

Switchover from transmission mode to reception mode ensues with a transmission-reception diplexer 6. The radio-frequency antenna 4 radiates the radio-frequency pulses into the measurement volume M for excitation of the nuclear spins and samples resulting echo signals. The acquired nuclear magnetic resonance signals are phase-sensitively demodulated in the reception channel 8 of the radio-frequency system 22 and converted into a real part and an imaginary part of the measurement signal in a respective analog-digital converter. An image is reconstructed by an image computer 17 from the measurement data so acquired. The administration of the measurement data, the image data and the control programs ensues via a system computer 20. Based on control programs, the sequence controller 18 monitors the generation of the respectively desired pulse sequences and the corresponding sampling of k-space. The sequence controller 18 controls the time-accurate switching of the gradients, the emission of the radio-frequency pulses with defined phase and amplitude and the receipt of the magnetic resonance signals. The time base for the radio-frequency system 22 and the sequence controller 18 is provided by a synthesizer 19. The selection of corresponding control programs for generation of a nuclear magnetic resonance image as well as the representation of the generated magnetic resonance image ensues via a terminal 21 that has a keyboard as well as one or more screens.

General Theory of the Circulating RF Excitations:

Conventional Body Coil Excitation

Figure 2:
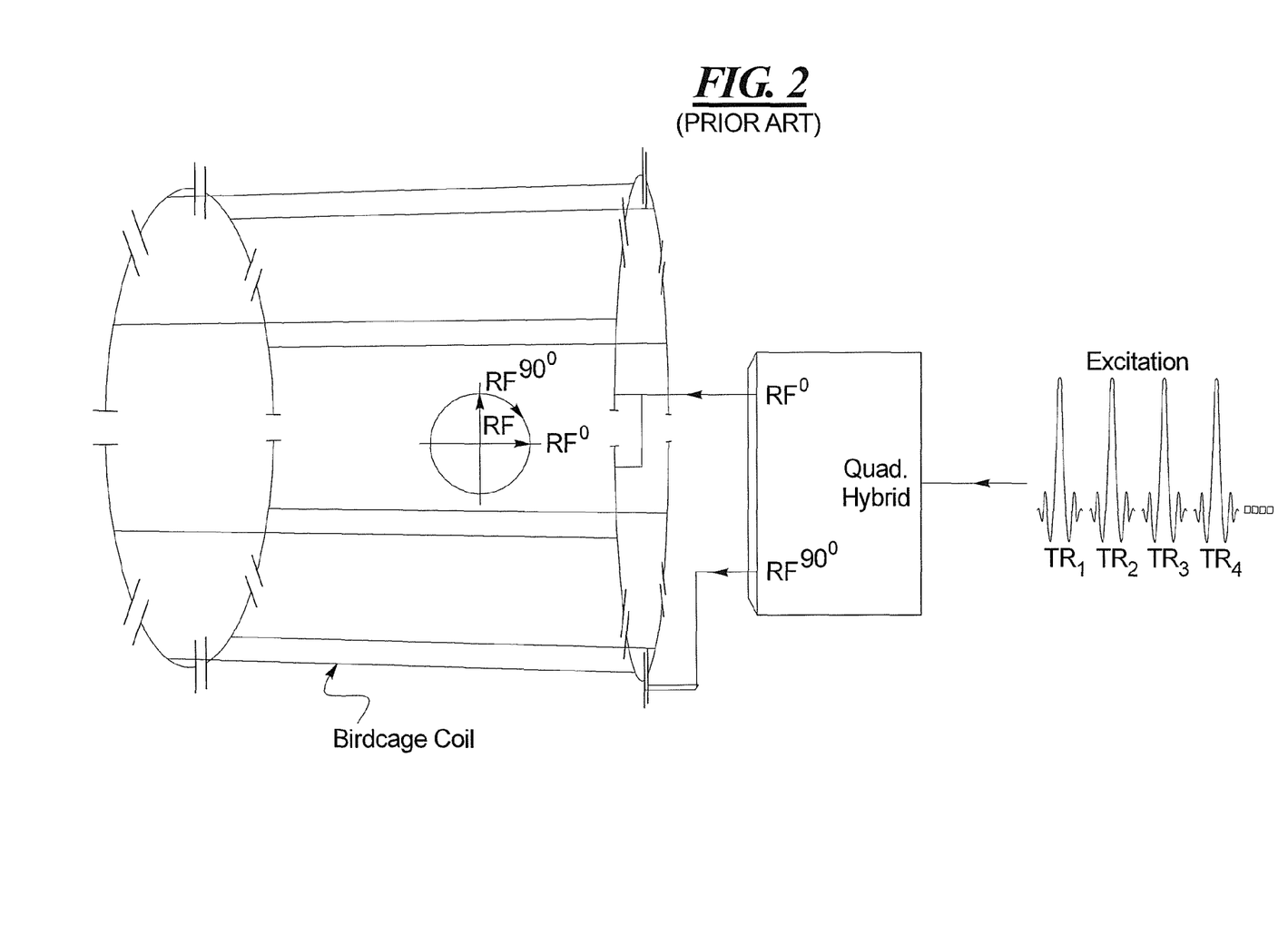
FIG. 2 schematically illustrates standard excitation in a magnetic resonance system using a conventional body coil and RF pulse scheme.

A body birdcage coil has two orthogonal channels. If only one channel is excited, a linearly polarized magnetic field is created in x or y direction. As shown in FIG. 2, conventionally a quadrature hybrid is used to deliver the excitation signal through single channel (Hayes C E, Edelstein W A, Schenck J F, Mueller O M, Eash M. An efficient, highly homogenous radiofrequency coil for whole-body NMR imaging at 1.5 T. J Magn Reson 1985; 63.:622-628). The quadrature hybrid divides the signal into two with equal magnitude and 90° phase difference which generates a forward polarized field. This rotational excitation is two times more efficient in total body SAR and four times better in peak SAR than a linear excitation.

Changing RF Fields

A transmit array system can be used to deliver the modified RF excitations to two channels of body birdcage coil, in which quadrature hybrid was eliminated. By modifying conventional sequences a linearly polarized RF excitation could be obtained instead of forward polarized.

Figure 3:
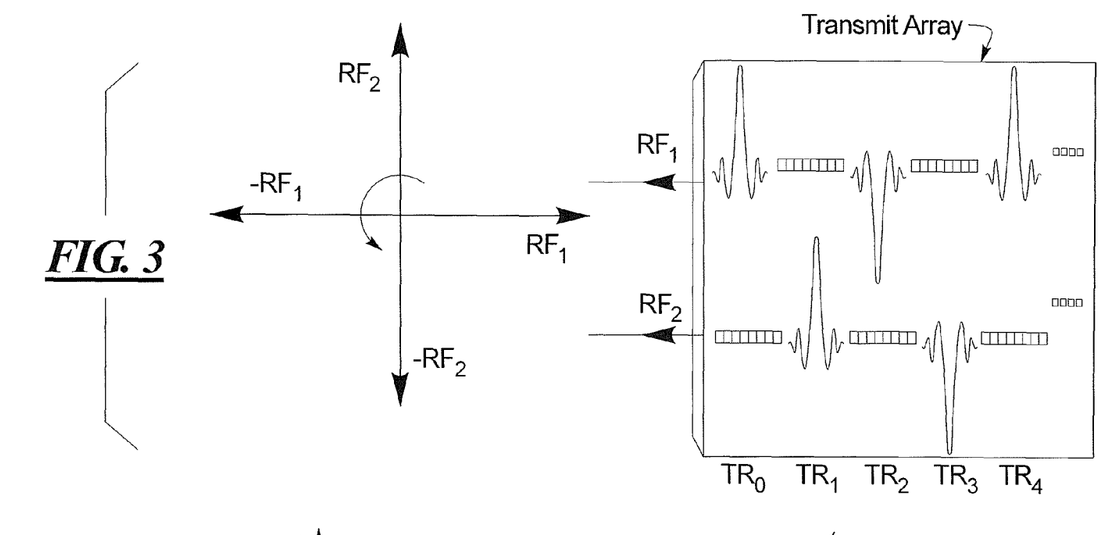
FIG. 3 schematically illustrates a modified RF excitation scheme and the birdcage coil field using the transmit array system operated in accordance with the present invention.

In conventional MR imaging, RF excitation scheme constant throughout a sequence. Although it is not easy to figure out the results of arbitrary modifications of RF excitations, effects of periodic changes can be calculated using Fourier theorem. FIG. 3 shows the modified linearly polarized RF excitation scheme in which the RF amplitudes and phases are changed to obtain a circulation that progresses by $\pi/2$ at each TR. Four different magnetic fields were created periodically such that $B_p = B_{p+4}$, where p is the index of the TR. Changing the direction of the linear polarization at each TR causes a circulation of excitation vector in counter-clockwise direction. At the first TR, the first RF channel on x-axis, $RF_1$ is on and $RF_2$ is off, as a result, the direction of the linear excitation field is on the x-axis. The second RF channel is on at the next TR and the vector is on the y-axis with a relative phase of $\pi/2$. At the third TR, $RF_1$ is on but with relative phase of $\pi$. Lastly, at the fourth TR, $RF_1$ is on the −y direction with a phase of $3\pi/2$. In this periodic scheme, magnetic field result of the $p^{th}$ excitation can be shown as $B_p = Be^{jp\pi/2}$, where B is the reference complex magnetic field expression. Using Fourier theorem one can conclude that phase modulation in k-space results with shift in image domain. The modulation causes $N_y/P$ pixels shift in image domain, where $N_y$ is the number of phase encoding lines, P is the period of the circulating excitation and equals to four in above case (FIG. 3).

Effect of Changing RF Fields on the ICRF Coil

Figure 4A:
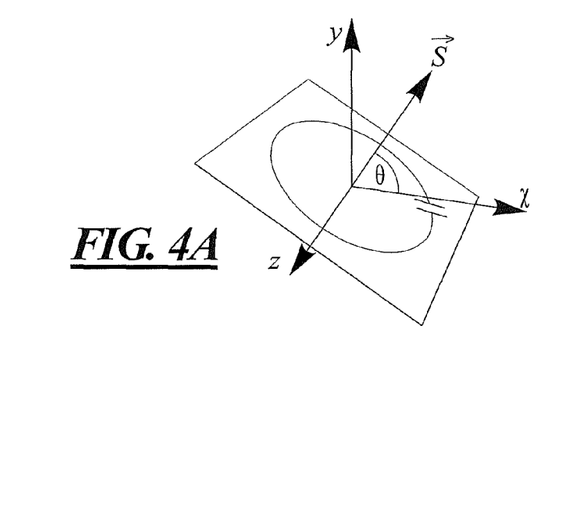
FIG. 4a shows an ICRF coil oriented at an angle θ, and FIG. 4b schematically illustrates the corresponding linearly polarized RF field and the ICRF coil.
Figure 4B:
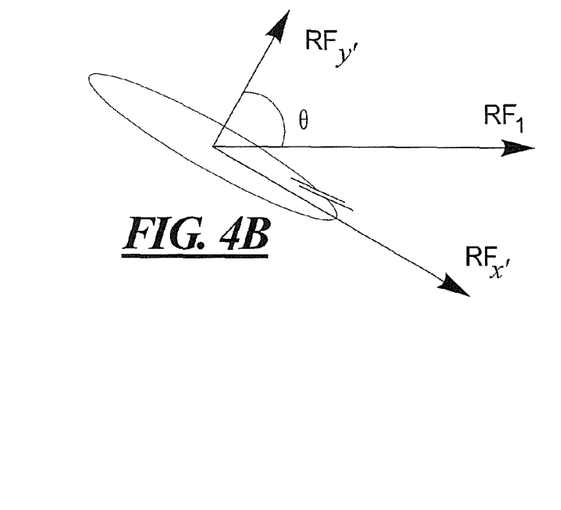

On the other hand, an ICRF coil is exposed to a different coupling mechanism. The magnetic field transmitted by a body coil induces current on the ICRF coil and this current causes a secondary field. When the excitation field is linear, coupling of the transmit field and ICRF coil is directly related to its orientation. FIGS. 4a and 4b show the relation of the ICRF coil orientation and the excitation vector. As an example, it is assumed that $RF_1$ is applied and the ICRF coil is tilted as shown in FIG. 4a such that the surface normal vector of the ICRF coil makes θ angle with $RF_1$. This excitation pulse can be decomposed into two orthogonal fields, $RF_{x'}$ and $RF_{y'}$ shown in FIG. 4b which are perpendicular and parallel components to surface normal vector of the ICRF coil, respectively. Using Faraday's law of induction, it can be concluded that only the $RF_{y'}$ induces a current on the ICRF coil, but $RF_{x'}$ does not. Therefore, the effective magnetic field component is B cos θ and the secondary field produced by the ICRF coil becomes:

$$B_{ICRF,1}=BC \cos \theta$$

where C is complex amplification factor due to the ICRF coil.

If one applies this operation to other components of the RF excitation pulses in FIG. 3, magnetic fields due to excitation profile become $B_{ICRF,2}=BC \sin \theta$, $B_{ICRF,3}=-BC \cos \theta$, and $B_{ICRF,4}=-BC \sin \theta$. This excitation profile is periodic, but it is not as simple as the previous case, because not only phase but also amplitude modulation are operating. A simpler form of them can be obtained by decomposing each excitation:

$$B_{ICRF,1}=BC \cos \theta = BC\alpha + BC\beta$$

$$B_{ICRF,2}=BC \sin \theta = BC\alpha e^{i\pi/2} + BC\beta e^{i3\pi/2}$$

$$B_{ICRF,3}=-BC \cos \theta = BC\alpha e^{i\pi} + BC\beta e^{i\pi}$$

$$B_{ICRF,4}=-BC \sin \theta = BC\alpha e^{i3\pi/2} + BC\beta e^{i\pi/2}$$

Above, $\alpha=(\cos \theta + i \sin \theta)/2$ and $\beta=(\cos \theta - i \sin \theta)/2$. One can express $p^{th}$ excitation in a sequence as $B^*_p = BC\alpha e^{i(p-1)\pi/2} + BC\beta e^{-i(p-1)\pi/2}$. Therefore, the resultant image consists of two copies of the original ICRF coil image. The first image shifts in phase encoding direction and stays in the anatomy. The second image is called "ghost" and shifted to the opposite direction, which enables tracking of the ICRF coil. Furthermore, their ratio is constant and phase of this ration equals to two times of the ICRF coil orientation, 2θ, which paves the way of calculating rotational orientation of the ICRF coil simultaneously Small-Tip Angle Approximation:

The general theory of the invention is given above. Furthermore, small tip angle approximation can be used for detailed formulation and analysis. Assume $M_{T,Anatomy}$ is spin magnetization of the anatomy and signal resulting from a conventional sequence can be expressed as:

$$S_{Anatomy}(t) = \iint (M_{T,Anatomy}) e^{-i2\pi k_x x} e^{-i2\pi k_y y} dx dy \quad [4]$$

where $k_x$ and $k_y$ are spatial frequency variables in x and y directions respectively.

The generalized magnetization after the $p^{th}$ RF (or $p^{th}$ TR) is:

$$M_{pT,Anatomy}^+(t) = M_{T,Anatomy} e^{ip\pi/2} \quad [5]$$

Assuming y as the phase encoding direction, p can be expressed in terms of imaging parameters as:

$$p = k_y N_y \Delta y \quad [6]$$

Above, $\Delta y$ is the image resolution in phase encoding direction. Substituting Eq. [6] into Eq. [4]. gives:

$$S_{Anatomy}(t) = \iint (M_{T,Anatomy} e^{-i2\pi k_y (y - N_y \Delta y/4)}) e^{-i2\pi k_x x} dx dy \quad [7]$$

Eq. [7] states that the modified RF excitation causes a shift of the image location in phase encoding direction with an amount of $N_y/P$.

As stated above in the general theory of the method, the effect of the circulating linear polarization vector to the ICRF coil is more complex than the anatomy. The transmit field induces current on the ICRF coil and the induced current creates a secondary magnetic field. This time dependent magnetic field created by the ICRF coil can be represented as:

$$\vec{B}_{ICRF,t}(t) = I_{ICRF,t}(t) \vec{B}_{ICRF}' \quad [1]$$

where $I_{ICRF,t}(t)$ is the time dependent current due to transmit field and expressed as:

$$I_{ICRF,t}(t) = B_t(t) \cos(\omega_o t + \sigma) \hat{a}_t \cdot \vec{s} \quad [2]$$

Above, $B_t(t)$ is peak value of time dependent transmit magnetic field envelope function, $\omega_o$ is the Larmor frequency, σ and $\hat{a}_t$ are the phase and unit vector of $B_t(t)$, and $\vec{s}$ is surface normal vector of the ICRF coil, given by:

$$\vec{s} = s(\cos \theta \hat{a}_x + \sin \theta \hat{a}_y) \quad [3]$$

where s is the area of the ICRF coil. For every different RF excitation, the dot product of the surface normal vector of the ICRF coil and the unit vector of the transmit magnetic field (Eq. [2]) causes different complex parameter.

In Eq. [1], $\vec{B}_{ICRF}'$ is the peak value of magnetic field generated by the ICRF coil at a point of interest when a unit current is applied to an imaginary terminal of the coil:

$$\vec{B}_{ICRF}' = B_{co}(\cos(\theta + \eta) \hat{a}_x + \sin(\theta + \eta) \hat{a}_y) \quad [4]$$

Above, $B_{co}$ is the magnitude of the magnetic field, θ+η is the orientation of the magnetic field vector at the point of interest, η is the phase term of the magnetic field related to other than the orientation of the ICRF coil. Note that, the field vector orientation is directly related to the orientation of the ICRF coil, therefore θ appears in the magnetic field expression. Using above equations, x and y components of the $\vec{B}_{ICRF,t}(t)$ can be expressed as:

$$B_{ICRF,tx}(t) = B_t(t) B_{co} s [\hat{a}_t \cdot (\cos \theta \hat{a}_x + \sin \theta \hat{a}_y)] \cos(\omega_o t + \sigma) \cos(\theta + \eta)$$

$$B_{ICRF,ty}(t) = B_t(t) B_{co} s [\hat{a}_t \cdot (\cos \theta \hat{a}_x + \sin \theta \hat{a}_y)] \cos(\omega_o t + \sigma) \sin(\theta + \eta) \quad [5]$$

Converting the lab frame expressions into the rotating frame will be useful for calculations (15):

$$B_x^+(t) = B_{ICRF,tx}(t) \cos(\omega_o t) + B_{ICRF,ty}(t) \sin(\omega_o t)$$

$$B_y^+(t) = -B_{ICRF,tx}(t) \sin(\omega_o t) + B_{ICRF,ty}(t) \cos(\omega_o t) \quad [6]$$

where $B_x^+(t)$ and $B_y^+(t)$ are the x and y components of the positively rotating frame. Ignoring $2\omega_o t$ components, which are not effective in NMR:

$$B_x^+(t) = -B \cos(\theta + \eta) \sin \sigma + B \sin(\theta + \eta) \cos \sigma$$

$$B_x^+(t) = -B \sin(\theta + \eta) \cos \sigma + B \sin(\theta + \eta) \sin \sigma \quad [7]$$

Above, $B = B_t(t) B_{co} s [\hat{a}_t \cdot (\cos \theta \vec{a}_x + \sin \theta \vec{a}_y)]/2$.

These rotating frame components are enough to express magnetizations. For the sake of simplicity, assume a small tip angle to obtain x and y components of the magnetization:

$$dM_x^+(t)/dt \approx -\gamma M_o B_y^+(t)$$

$$dM_y^+(t)/dt \approx \gamma M_o B_x^+(t) \quad [8]$$

where $\gamma$ is gyromagnetic ratio, $M_o$ is the instantaneous magnetic moment per sample voxel immediately after applying a 90° pulse. Note that, later in this section it will be shown that the formulation is still valid for larger flip angles using a computer simulation (16). Assuming a square pulse:

$$M_x^+(t) = -\gamma \tau M_o B_y^+(t)$$

$$M_y^+(t) = \gamma \tau M_o B_x^+(t) \quad [9]$$

Above, $\tau$ is the duration of the pulse. Complex transverse magnetization of the ICRF coil magnetic field can be written as $M_{T,ICRF}^+(t) = M_x^+(t) + iM_y^+(t)$ and substituting Eq. [9] gives:

$$M_{T,ICRF}^+(t) = M_{T,ICRF} e^{i\theta}[\hat{a}_t \cdot (\cos\theta \hat{a}_x + \sin\theta \hat{a}_y)] \quad [10]$$

where $M_{T,ICRF} = \gamma \tau M_o e^{i\eta} e^{i\omega} B_t(t) B_{co} s/2$. Remaining terms at the right side of Eq. [10] are directly related to the orientation of the ICRF coil. As the RF pulse scheme changes, the complex transverse magnetization of the ICRF coil changes similar to the anatomy case. However, the orientation related complex term in Eq. [10] makes a very important difference. At the first TR, unit vector of the transmit magnetic field will be $\hat{a}_t = \hat{a}_x$, because its direction shows the x-axis. Substituting this information to Eq. [10] results with the first complex transverse magnetization of the ICRF coil as:

$$M_{OT,ICRF}^+(t) = M_{T,ICRF} e^{i\theta} \cos\theta \quad [11]$$

The second, third, and the forth transmit magnetic field unit vectors become $\hat{a}_y$, $-\hat{a}_x$, and $-\hat{a}_y$ respectively and one can generalize the $p^{th}$ RF as:

$$M_{pT,ICRF}^+(t) = M_{T,ICRF}(e^{i2\theta} e^{ip\pi/2} + e^{-ip\pi/2})/2 \quad [12]$$

The above equation states that the modified RF pulse scheme adds a phase term $(e^{i2\theta} e^{ip\pi/2} + e^{-ip\pi/2})/2$ to the ICRF signal. Also, not only the phase, but also the magnitude of the effective RF field changes in each TR.

For the particular case explained above, the signal expression can be given as:

$$S_{ICRF}(t) = \iint (M_{T,ICRF}(e^{i2\theta} e^{ip\pi/2} + e^{-ip\pi/2})) e^{i2\pi(k_x x + k_y y)} dxdy/2 \quad [13]$$

Substituting Eq. [6] into Eq. [13] gives:

$$S_{ICRF}(t) = \iint M_{T,ICRF} e^{-i2\pi k_y (y - N_y \Delta y/4)} e^{-i2\pi k_x x} dxdy/2 + \iint (M_{T,ICRF} e^{i2\theta}) e^{-i2\pi k_y (y + N_y \Delta y/4)} e^{-i2\pi k_x x} dxdy/2 \quad [14]$$

Two important conclusions can be made based on this result and Eq. [14]. First, the modified RF scheme causes shifting of the original image. The anatomy shifts in phase encoding direction with an amount of $N_y/4$ pixels, on the other hand the original ICRF coil image shifts in phase encoding direction and the ghost shifts in reverse direction. As a result, the original ICRF coil image stays in the anatomy and the ghost of the ICRF coil image shifts to the opposite direction. This enables the separation of the ICRF coil image from the anatomy image, so that the ICRF coil image can be color-coded and placed into the anatomy image and the catheter can be tracked. Secondly, Eq. [14] states that the phase difference of the ICRF coil and ghost images is equal to two times of the rotational orientation angle of the ICRF coil, $2\theta$.

In the following, it is assumed that $y_o$ is the central line between the ICRF coil image and the ghost. Although the exact location of the original image is not known, $y_o$ is related to the total number of phase lines and number of pulses in one turn and given by $y_o = N_y - 2N_y/P$. As a result, for the particular case where P=4, $y_o$ equals to the center row of the image $N_y/2$. A more general formula for an arbitrary P, the anatomy and ICRF coil signals can be expressed as:

$$S_{Anatomy}(t) = \iint M_{T,Anatomy} e^{-i2\pi k_y (y - N_y \Delta y/P)} e^{-i2\pi k_x x} dxdy \quad [15]$$

$$S_{ICRF}(t) = \iint M_{T,ICRF} e^{-i2\pi k_y (y - N_y \Delta y/P)} e^{-i2\pi k_x x} dxdy/2 + \iint (M_{T,ICRF} e^{i2\theta}) e^{-i2\pi k_y (y + N_y \Delta y/P)} e^{-i2\pi k_x x} dxdy/2$$

Eq. [15] states that the shift is $N_y/P$ pixels, therefore number of shifting pixels can be adjusted by changing the number of circulation. For example the amount of shifting can be increased by decreasing the value of P and vice versa. Moreover, if the circulation direction is switched to clock-wise direction, the anatomy and ICRF coil images shift opposite directions.

Figure 5:
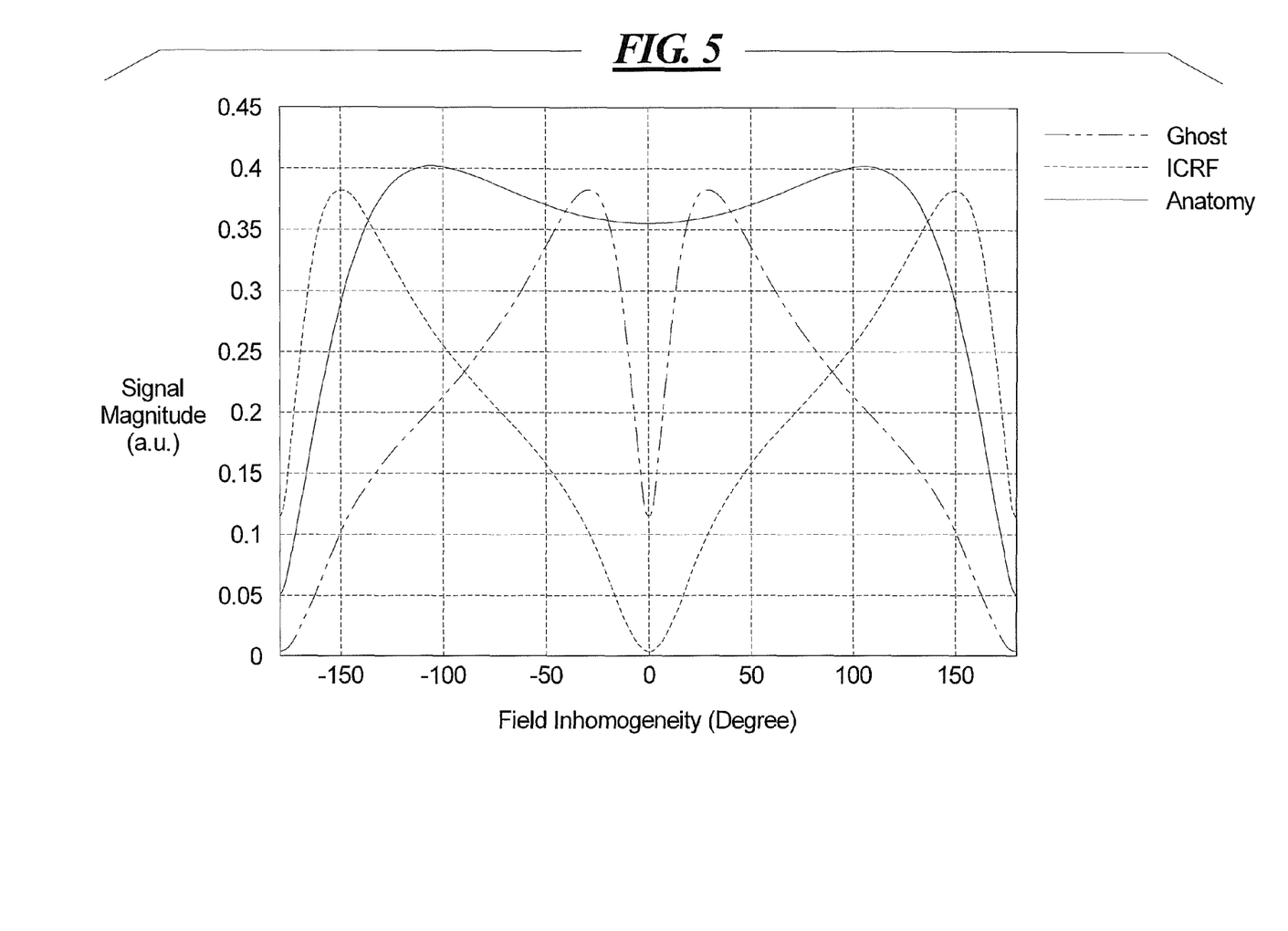
FIG. 5 illustrates experimental results in accordance with the inventive method, using a TrueFISP sequence.

Sequences:

The presented technique was applied to two fast sequences FLASH and TrueFISP. A MATLAB simulation code for TrueFISP sequence is used to show the shifting mechanism is still valid for larger flip angles. TrueFISP sequence is highly dependent on field inhomogeneities. In order to understand signal behaviors of the anatomy and the ICRF coil computer simulations were conducted using MATLAB. The anatomy and catheter signals were obtained using following parameters: T1 200 ms, T2 60 ms, TR 5.8 ms, TE 2.9 ms, flip angle 50°. FIG. 5 shows the simulation where the ICRF coil, ghost, and anatomy can be seen. Furthermore, TrueFISP sequence is based on gradient echo imaging principles but steady state signal varies drastically. FIG. 5 shows that the anatomy, ICRF coil, and ghost signals differ significantly as a function of field inhomogeneity. Also, the ICRF coil and its ghost have the same shape against the field homogeneity, but there is 180° phase difference. This property introduces another parameter for the method, because; signal adjusting field inhomogeneity can change amplitudes of the ICRF coil and its ghost.

Method:

As noted above, an object of the inventive method is to i) separate the anatomy and interventional devices and ii) find their rotational orientation using a linearly polarized body birdcage coil. The identical RF pulse shape with changing amplitude and phase is used to excite the body birdcage coil. The quadrature hybrid is eliminated and the body coil is used as a two channel linear transmit-only coil. FLASH and True-FISP sequences are modified and circulating linearly polarized field is delivered using the transmit array system.

In substantiating the implementation of the inventive method, a 3 tesla Siemens TIMTrio and an 8-channel transmit array systems were used. Siemens body and spine matrix coils are used for reception. A MATLAB (version 7.6; Mathworks Inc., Natick Mass.) code is written for the reconstruction, calculation of the rotational orientation and as well as the color-coding.

Figures 6A, 6B:
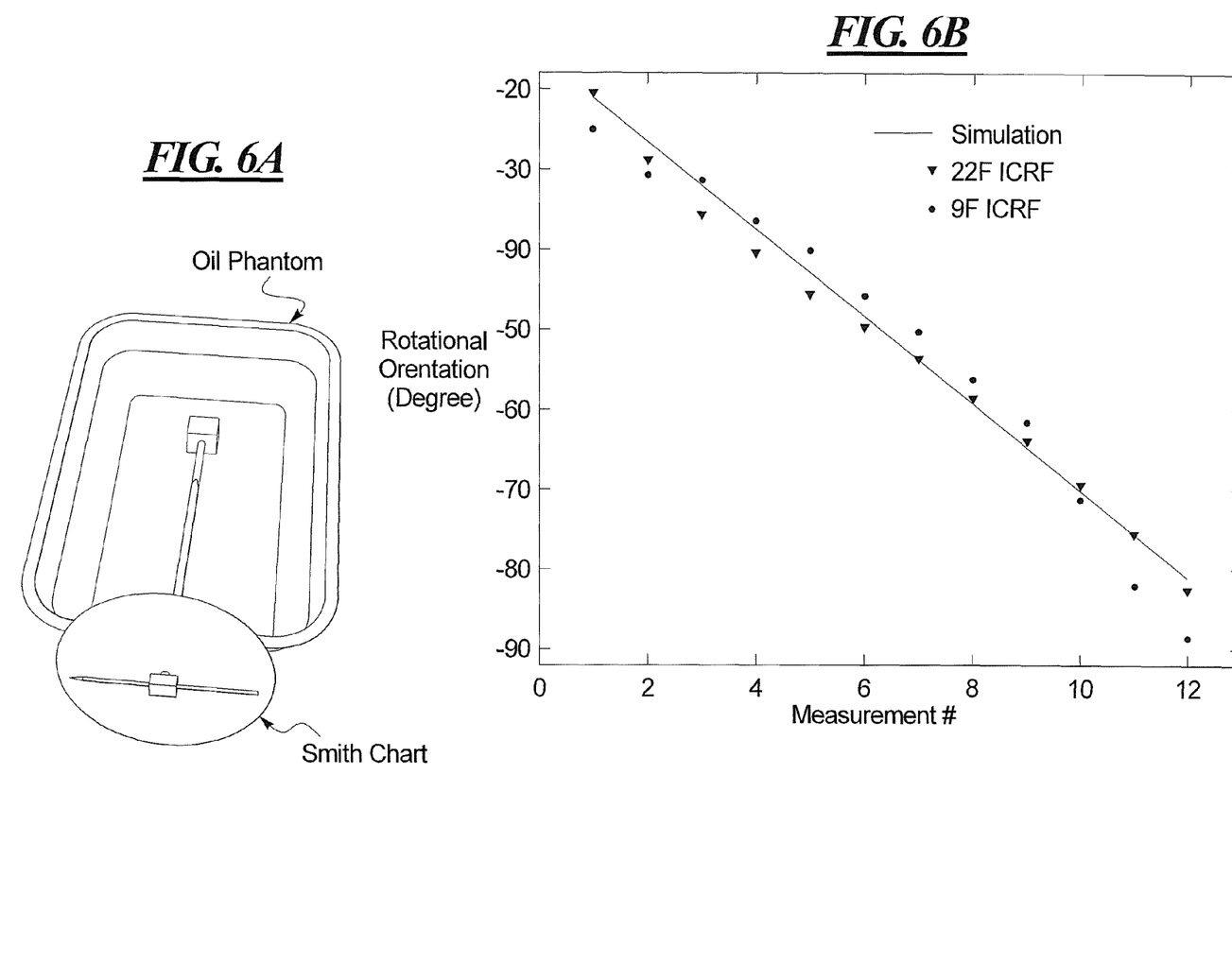
FIG. 6a schematically illustrates an oil phantom used to experimentally verify the inventive method.
FIG. 6b shows the experimental result.

Rotational Orientation:

Two different ICRF coils with different diameters, and the same length were constructed for the rotational orientation experiments. The first ICRF was 100-mm long and constructed on a 6F Teflon catheter using coated copper wire 0.4 mm in diameter; a heat shrink tube was used for isolation resulting in a prototype device with an outer diameter of 3 mm (9F). It was tuned by a 18 pF ceramic chip capacitor (ATC, Huntington Station, N.Y., USA) to 123.23 MHz using an HP 8753D network analyzer (Agilent Technologies, Santa Clara, Calif., USA). The second ICRF coil had the same length with 22F total diameter. A rectangular 15×10×30 cm$^3$ oil phantom was constructed. A Smith chart was used to change rotational angle (FIG. 6a). Before each acquisition, the ICRF coils were rotated equally.

FLASH experiment simulation was done for changing rotational orientation of the ICRF coil for proof of principle. In order to find the phase difference between the ICRF coil and ghost images, phase contrast algorithm (Bernstein M A, Grgic M, Brosnan T J, Pelc N J. Reconstructions of phase contrast, phased array multicoil data. Magn Reson Med 1994; 32(3):330-334) was used. For P=4 case, the center of the image is the border of the shifted images. Cutting one side and multiplying with the conjugate of the other side of the image provides weighting. Phase of the mean value gives the weighted average's phase, which is two times of the absolute orientation of the ICRF coil.

Catheter Tracking:

The first ICRF coil, 9F, was also used in imaging experiments. The ICRF coil is used similar to the study (Celik H, Uluturk A, Tali T, Atalar E. A catheter tracking method using reverse polarization for MR-guided interventions. Magn Reson Med 2007; 58(6):1224-1231). The same oil phantom box was used and four KCl solution filled straws are inserted with the ICRF coil.

Flash

Flash sequence is modified to get circulating polarizations with following parameters: TR 9.8 ms, TE 4.1 ms, slice thickness 5 mm, flip angle 30°, FOV 300×300, imaging matrix 256×256, TrueFISP In addition, proof of principle experiments were conducted with a modified TrueFISP sequence using following parameters was used: TR 5.8 ms, TE 2.9 ms, slice thickness 5 mm, flip angle 50°, imaging matrix 256×256.

Transmit Array Calibration

Two channels of the transmit array system have been used for the experiments described herein. After each system boot different phase offsets between the channels have been observed. Therefore, before each experiment, the phase difference is calibrated using the reverse polarized mode of the birdcage coil. As spins are forward polarized, if the body birdcage coil is adjusted to produce the reverse polarization mode, no signal can be received. The reverse polarization mode is obtained by two RF pulses with the same amplitude and a 90° phase difference. Before the experiments, phase of the y-channel is scanned between 40° to 140° with 10° increment. The image with a minimum signal level is assumed to be the reverse polarized mode of the image. After fine-tuning, the relative phase difference between the x- and y-channels is found.

Rotational Orientation of the ICRF Coil

FIG. 6a shows rotational orientation experiment (oil bath) setup using a Smith chart and FIG. 6b the results obtained using two different ICRF coils. In each measurement, one of the ICRF coils rotated one unit, which is approximately equal to 5°. The experiment was repeated for both ICRF coils. Maximum deviation from the simulation is 8.6°. Although smaller size ICRF coils have lower quality factors and signal amplifications, result for the 9F catheter is very similar.

Tracking of the ICRF coil

Figure 7A:
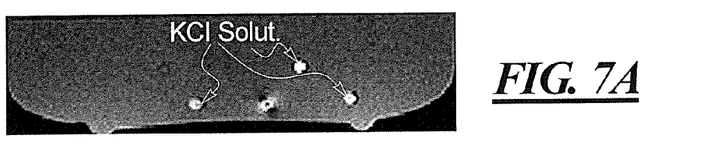
Figure 7B:
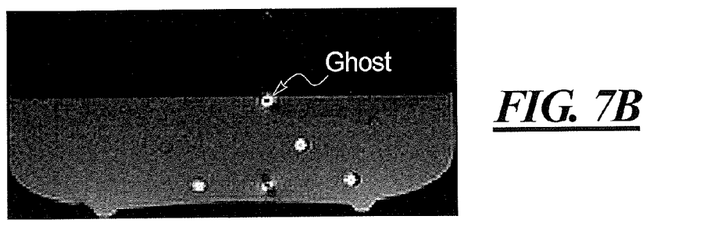
Figure 7C:
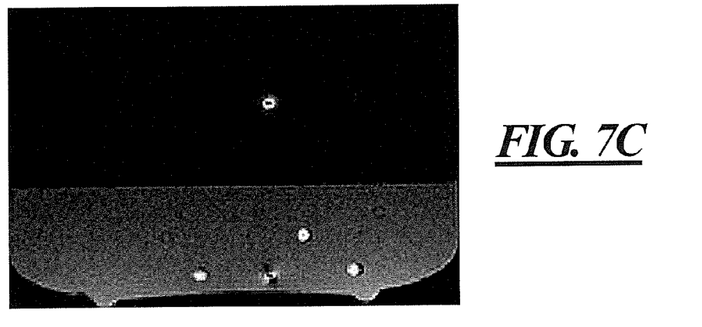

In the section above describing the underlying theory, the period of the circulation, P, was assumed to be four as an example. Moreover, number of shifting pixels can be adjusted by changing the period. FIG. 7a shows the original image without shifting as a reference where $N_y$=256 and obtained using FLASH sequence. There are three straws filled with water and the inventive method successfully separates the ICRF coil image from the phantom in all cases. In FIG. 7b, P is 16, and images separated 32 pixels. Lastly, FIG. 7c shows 64 pixels separated images with P equals to 16.

Figure 8A:
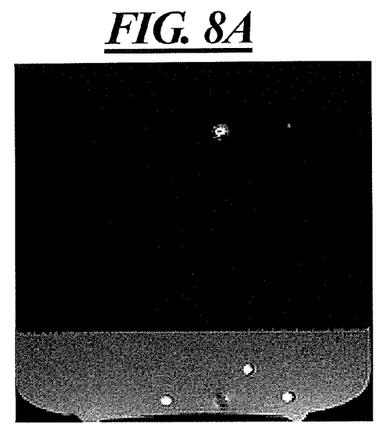
FIGS. 8a, 8b and 8c are images obtained in accordance with the inventive method to illustrate the effect of changing the circulating direction of the polarization vector.
Figure 8B:
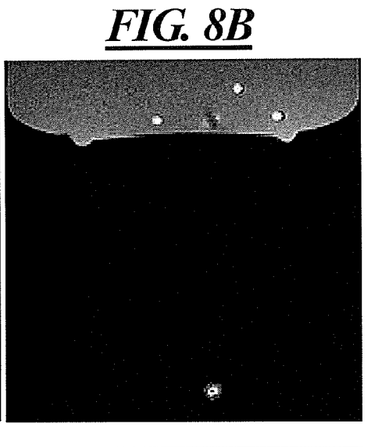
Figure 8C:
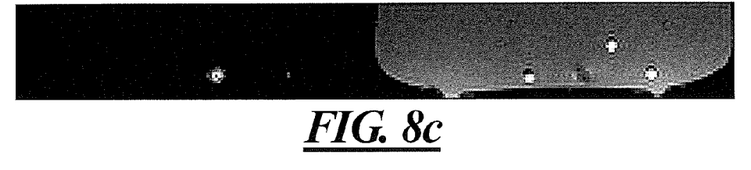

There are two other important parameters to change characteristics of the shifting. One of them is circulating direction of the polarization vector. FIG. 8a shows an image of counter-clockwise circulation of the vector with P=4. Shifting the circulation direction to clock wise direction swaps the anatomy image and the ghost (FIG. 8b). Furthermore, phase encoding direction is A-P in FIGS. 8a and 8b. Changing the phase encoding direction to L-R changes the whole image (FIG. 8c). As a result, there are three significant parameters to be manipulated according to application or imaging plane: P, vector circulation and phase encoding directions.

The method works with different imaging planes such as Coronal, sagittal, and oblique for P=4.

CONCLUSION

As described above, the field created by the ICRF coil depends on the direction of the linearly polarized transmit field (FIG. 5). This fact is the basis of the method. In the case of anatomical images, there is only the phase modulation and this causes the shift of the anatomy image. However, as the phase of the RF excitation field changes, not only the phase but also the amplitude of the ICRF coil field created varies. Furthermore, both phase and magnitude modulation mechanisms occur different than the anatomy case. The modulations in the k-space can be calculated analytically or by a computer simulation.

A similar modulation of the phase and the magnitude occurs when a wire is used instead of an ICRF coil, because the current induced on the wire is also dependent on the phase of the excitation field. As the phase of the excitation changes, the phase of the current on the wire changes and as a result, field profile at the vicinity of the wire changes. This disturbance affects the k-space lines and a similar shifting occurs as the ICRF coil case.

As is apparent from the above description, the basic requirement of the tracked item is that it be electrically conductive. The aforementioned wire can be configured as a receive-coupled RF coil, a straight wire, a bent wire, a guidewire, or a self-resonating structure such as a self-resonating loop. The tracked item may also be a medical interventional device or a medical implant.

In the experimental substantiation, the x-channel of the body coil performed significantly worse than the y-channel. Therefore, oil was used in the phantom experiments, because it helped to avoid dielectric effect-related inhomogeneities. In addition, the same signal level from the individual body coil channels is obtained only when the y-channel is multiplied by 0.67, while the multiplier of the x-channel is kept at 1.00 using the transmit array system. Therefore, oil phantom is used to obtain the homogeneous reverse polarization mode of the image.

The main problem of the method for rotational orientation is symmetry of the ICRF coil in $\phi$ direction of cylindrical coordinates. Therefore, rotational orientation is $\pi$ symmetric and the method cannot discriminate θ° from θ°+180°.

As described above, a forward polarized excitation has a better SAR performs than a linear excitation. The linear polarization (FIG. 2) doubles average SAR and quadruples peak SAR. Nevertheless, this is not valid with modified circulating linear RF excitation. Its average body SAR is still two times more than forward excitation, but peak SAR is also two times more, because the electric field vector changes at a point of interest from TR to TR. For P=4, the electric field at a point drops such that SAR becomes two times of the forward polarization case. As a result, peak and average SAR of the modified circulating RF excitation is doubled as compared to conventional excitation. The conventional SAR calculation can be used and halving the limit keeps the new design in safety limits.

The method according to the invention can be used wherein the surrounding anatomy that surrounds the tracked item includes anatomy of a first type and an anatomy of a second type, with magnetic resonance signals emitted by the first type of anatomy being distinguishable from magnetic resonance signals emitted by the second type of anatomy. The magnetic resonance signals representing the first type of anatomy and the magnetic resonance signals representing the second type of anatomy can be processed so as to suppress representation of the anatomy of the first type in the resulting image.

In summary, in the inventive method, the rotational orientation of the ICRF coil is determined simultaneously with tracking the coil built on a catheter. The anatomy and the ICRF coil images are separated, then orientation is calculated and color-coded image of the ICRF coil is reconstructed for tracking. Phantom experiments have been demonstrated the method using both FLASH and TrueFISP sequences. The method can also be used with sequences for MR spectroscopy.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for tracking a tracked item in a patient comprising the steps of:

introducing a patient into a magnetic resonance data acquisition unit comprising a radio frequency (RF) transmit array system comprising an RF radiator having an RF radiator structure configured as a birdcage antenna, said patient, before or after introduction into the data acquisition unit, having an electrically conductive item, selected from the group consisting of a wire and an ICRF coil, located therein to be tracked as a tracked item;

operating the magnetic resonance data acquisition unit to acquire magnetic resonance data from the patient introduced therein inside the birdcage antenna, including operating said birdcage antenna by providing a plurality of different RF transmission profiles thereto in a plurality of data acquisition repetition times, said plurality of different RF transmission profiles causing said birdcage antenna to radiate a linearly polarized RF field that circulates by progressing through different field directions in the respective repetition times, and thereby causing the tracked item and anatomy in the subject surrounding the tracked item to behave differently as said field direction changes by inducing a current in said tracked item that has a phase that changes dependent on said different field directions, and thereby also causing said tracked item and said surrounding anatomy to emit magnetic resonance signals that are distinguishable from each other;

in a computerized processor, processing said magnetic resonance signals from said tracked item and said surrounding anatomy to produce an electronic data file representing an image, in which said tracked item and said surrounding anatomy are distinguishable from each other and in which a rotational orientation and position of said tracked item with respect to said surrounding anatomy are also visible;

providing said electronic data file from said processor to a display in communication with said processor and, at said display, displaying said image represented by said electronic data file.

2. A method as claimed in claim 1 comprising employing a straight wire as said tracked item.

3. A method as claimed in claim 1 comprising employing a bent wire as said tracked item.

4. A method as claimed in claim 1 comprising employing a guidewire as said tracked item.

5. A method as claimed in claim 1 comprising employing a two channel body coil as said RF transmit array system.

6. A method as claimed in claim 1 comprising employing a multiple channel transmit coil as said RF transmit array system.

7. A method as claimed in claim 1 comprising employing a multiple channel coil system as said RF transmit array system.

8. A method as claimed in claim 1 comprising employing a medical interventional device as said tracked item.

9. A method as claimed in claim 1 comprising employing a medical implant as said tracked item.

10. A method as claimed in claim 1 wherein said surrounding anatomy comprises anatomy of a first type and anatomy of a second type, with magnetic signals emitted by said anatomy of said first type being distinguishable from magnetic resonance signals emitted by said anatomy of said second type, and, in said computerized processor, processing magnetic resonance signals representing said anatomy of said first type and magnetic resonance signals representing said anatomy of said second type to suppress representation of said anatomy of said first type in said data file.

11. A magnetic resonance system for tracking a tracked item in a patient comprising:

a magnetic resonance data acquisition unit comprising a radio frequency (RF) transmit array system, comprising an RF radiator having an RF radiator structure configured as a birdcage antenna configured to allow introduction of a patient into the data acquisition unit, said patient, before or after introduction into the data acquisition unit, having an electrically conductive item, selected from the group consisting of a wire and an ICRF coil, located therein to be tracked as a tracked item;

a computerized control unit configured to operate the magnetic resonance data acquisition unit to acquire magnetic resonance data from the patient introduced therein inside the birdcage antenna, including operating said birdcage antenna by providing a plurality of different RF transmission profiles thereto in a plurality of data acquisition repetition times, said plurality of different RE transmission profiles causing said birdcage antenna to radiate a linearly polarized RF field that circulates by progressing through different field directions in the respective repetition times, and thereby causing the tracked item and anatomy in the subject surrounding the tracked item to behave differently as said field direction changes by inducing a current in said tracked item that has a phase that changes dependent on said different field directions, and thereby also causing said tracked item and said surrounding anatomy to emit magnetic resonance signals that are distinguishable from each other;

a computerized processor configured to process said magnetic resonance signals from said tracked item and said surrounding anatomy to produce an electronic data file representing an image in which said tracked item and said surrounding anatomy are distinguishable from each other and in which a rotational orientation and position of said tracked item with respect to said surrounding anatomy are also visible;

a display in communication with said processor, and said processor being configured to provide said electronic data file to said display to cause said image represented by said electronic data file to be displayed at said display.

12. A non-transitory computer-readable storage medium encoded with programming instructions, said storage medium being loadable into a computerized control and processing system of a magnetic resonance system, said magnetic resonance system comprising a magnetic resonance data acquisition unit comprising a radio-frequency (RF) transmit array system, comprising an RF radiator having an RF radiator structure configured as a birdcage antenna configured to allow introduction of a patient into the data acquisition unit, said patient, before or after introduction into the data acquisition unit, having an electrically conductive item, selected from the group consisting of a wire and an ICRF coil located therein to be tracked as a tracked item, said programming instructions, when said storage medium is loaded into said computerized control and processing system, causing said computerized control and processing system to:

operate the magnetic resonance data acquisition unit to acquire magnetic resonance data from the patient introduced therein inside the birdcage antenna, including operating said birdcage antenna by providing a plurality of different RF transmission profiles thereto in a plurality of data acquisition repetition times, said plurality of different RF transmission profiles causing said birdcage antenna to radiate a linearly polarized RF field that circulates by progressing through different field directions in the respective repetition times, and thereby causing the tracked item and anatomy in the subject surrounding the tracked item to behave differently as said field direction changes by inducing a current in said tracked item that has a phase that changes dependent on said different field directions, and thereby also causing said tracked item and said surrounding anatomy to emit magnetic resonance signals that are distinguishable from each other;

process said magnetic resonance signals from said tracked item and said surrounding anatomy to produce an electronic data file representing an image in which said tracked item and said surrounding anatomy are distinguishable from each other and in which a rotational orientation and position of said tracked item with respect to said surrounding anatomy are also visible;

provide said electronic data file to a display to cause the image represented by said electronic data file to be displayed at said display.

* * * * *